US008282559B2

United States Patent
Njemanze

(10) Patent No.: US 8,282,559 B2
(45) Date of Patent: Oct. 9, 2012

(54) METHOD FOR INDUCING AND MONITORING LONG-TERM POTENTIATION AND LONG-TERM DEPRESSION USING TRANSCRANIAL DOPPLER ULTRASOUND DEVICE IN HEAD-DOWN BED REST

(76) Inventor: Philip Chidi Njemanze, Owerri (NG)

( * ) Notice: Subject to any disclaimer, the term of this patent is extended or adjusted under 35 U.S.C. 154(b) by 1582 days.

(21) Appl. No.: 11/715,894

(22) Filed: Mar. 9, 2007

(65) Prior Publication Data

US 2008/0221452 A1    Sep. 11, 2008

(51) Int. Cl.
*A61B 8/00* (2006.01)
(52) U.S. Cl. .................. 600/454; 600/453; 600/504
(58) Field of Classification Search .......... 600/453, 600/454, 504
See application file for complete search history.

(56) References Cited

U.S. PATENT DOCUMENTS

| | | | |
|---|---|---|---|
| 6,353,949 B1 * | 3/2002 | Falbo | 5/610 |
| 6,390,979 B1 * | 5/2002 | Njemanze | 600/438 |
| 2002/0062078 A1 * | 5/2002 | Crutchfield et al. | 600/453 |
| 2004/0158155 A1 * | 8/2004 | Njemanze | 600/454 |

* cited by examiner

*Primary Examiner* — Brian Casler
*Assistant Examiner* — Joseph M Santos

(57) ABSTRACT

The present invention provides a method for monitoring long-term potentiation and long-term depression, comprising placing a subject in head down bed rest position and monitoring in real-time cerebral mean blood flow velocity using a transcranial Doppler device during psychophysiologic tasks. The method involves using Fourier analysis of mean blood flow velocity data to derive spectral density peaks of cortical and subcortical processes. The effect of head-down bed rest at different time intervals is seen as accentuation of the cortical peaks in long-term potentiation and attenuation of subcortical peaks in long-term depression, relative to baseline. The effect of different interventions could be evaluated for research, diagnosis, rehabilitation and therapeutic use.

18 Claims, 5 Drawing Sheets

METHOD FOR INDUCING AND MONITORING LONG-TERM POTENTIATION AND LONG-TERM DEPRESSION USING TRANSCRANIAL DOPPLER ULTRASOUND DEVICE IN HEAD-DOWN BED REST

CROSS-REFERENCE RO RELATED APPLICATION

U.S. Patent Documents

| Document Number | Date | Name | Classification | Cited by |
|---|---|---|---|---|
| US 6,353,949 B1 | March 2002 | Falbo, Michael G. | 5/610 | Examiner |
| US 6,390,979 B1 | May 2002 | Njemanze, Philip C. | 600/438 | Examiner |
| US 2002/0062078 A1 | May 2002 | Crutchfield et al. | 600/453 | Examiner |
| US 2004/0158155 A1 | August 2004 | Njemanze, Philip C. | 600/454 | Examiner |
| US 11/636,554 | December 2006 | Njemanze Philip C. | | Inventor |

OTHER PUBLICATIONS

Boeijing a P. H., Mulder A. B., Pennertz C. M., Manshaden I., and Lopes Da Silva F. H. *Responses of the nucleus accumbens following fornix/fimbria stimulation in the rat. Identification and long-term potentiation of mono- and polysynaptic pathways*. Neuroscience, 1993; 53: 1049-1058.

Clapp W. C., Muthukumaraswamy S. D., Hamm J. P., Teyler T. J., and Kirk I. J. *Long-term enhanced desynchronization of the alpha rhythm following tetanic stimulation of human visual cortex*. Neuroscience Letters, 2006; 398: 220-223.

Frisén L. *Clinical Tests of Vision*. New York: Raven Press, 1990.

Ge Y. X., Xin W. J., Hu N. W., Zhang T., Xu J. T., and Liu X. G. *Clonidine depresses LTP of C-fiber evoked field potentials in spinal dorsal horn via NO-cGMP pathway*. Brain Research, 2006; 1118: 58-65.

Haghikia A., Mergia E., Friebe A., Eysel U. T., Koesling D., and Mittmann T. *Long-term potentiation in the visual cortex requires both nitric oxide receptor guanylyl cyclase*. Journal of Neuroscience, 2007; 27: 818-823.

Healy D. J. and Meador-Woodruff J. H. *Glutamatergic modulation of subcortical motor and limbic circuits. In: Advancing from the Ventral Striatum to the Extended Amygdala*. Ed: J. F. McGinty. New York: Annals of the New York Academy of Sciences, 1999; 877: 684-687.

Hu X. D., Ge Y. X., Hu N. W., Zhang H. M., Zhou L. J., Zhang T., Li W. M., Han Y. F., and Liu X. G. *Diazepam inhibits the induction and maintenance of LTP of C-fiber evoked field potentials in spinal dorsal horn of rats*. Neuropharmacology, 2006; 50: 238-244.

Ito, M. *Long-term depression*. Annual Review of Neuroscience, 1989; 11: 85-102.

Kamiya A., Iwase S., Michikami D., Fu Q., Mano T., Kitaichi K., and Takagi K. *Increased vasomotor sympathetic nerve activity and decreased plasma nitric oxide release after head-down bed rest in humans: disappearance of correlation between vasoconstrictor and vasodilator*. Neuroscience Letters, 2000; 281: 21-24.

Kang. H. S., Han M. H., Kwon B. J., Kwon O. K., Kim, S. H., and Chang K. H. *Evaluation of the lenticulostriate arteries with rotational angiography and 3D reconstruction*. American Journal of Neuroradiology, 2005; 26: 306-312.

Kelley A. E. *Functional specificity of ventral striatal compartments in appetitive behavior. In: Advancing from the Ventral Striatum to the Extended Amygdala*. Ed: J. F. McGinty. New York: Annals of the New York Academy of Sciences, 1999; 877: 71-90.

Lee T. J. *Sympathetic modulation of nitrergic neurogenic vasodilation in cerebral arteries*. Japanese Journal of Pharmacology 2002; 88: 26-31.

Njemanze P. C. *Cerebral lateralization for motor tasks in simulated microgravity. A transcranial Doppler technique for astronauts*. Journal of Gravitational Physiology, 2002; 9: 33-34.

Njemanze P. C. *Asymmetry of cerebral blood flow velocity response to color processing and hemodynamic changes during −6 degrees 24-hour head-down bed rest in men*. Journal of Gravitational Physiology, 2005; 12: 33-41.

Njemanze P. C. "*Asymmetric neuroplasticity of color processing during head down rest. a functional transcranial Doppler spectroscopy study*." Journal of Gravitational Physiology, 15(2):49-59, 2008.

Njemanze P. C. *Cerebral lateralization for facial processing: Gender-related cognitive styles determined using Fourier analysis of mean cerebral blood flow velocity in the middle cerebral arteries*. Laterality, 2007; 12: 31-49.

Okamura T. K., Ayajiki H., Fujioka K., Shinozaki K., and Toda N. *Neurogenic cerebral vasodilation mediated by nitric oxide*. Japanese Journal of Pharmacology, 2002: 88: 32-38.

Peters, M. *Description and validation of a flexible and broadly usable hand preference questionnaire*. Laterality, 1998; 3: 77-96.

Stroobant, N., and Vingerhoets G. *Transcranial Doppler ultrasonography monitoring of cerebral hemodynamics during performance of cognitive tasks. A review*. Neuropsychological Review 2000; 10: 213-231.

Teyler T. J., Hamm J. P., Clapp W. C., Johnson B. W., Corballis M. C., and Kirk I. J. *Long-term potentiation of human visual evoked responses*. European Journal of Neuroscience, 2005; 21: 2045-2050.

Thompson R. F. "*Brain: A Neuroscience Primer*", 3rd Edition, published in New York: Worth Publishers, 2000, p. 102-117.

STATEMENT REGARDING FEDERALLY SPONSORED RESEARCH OR DEVELOPMENT

Not Applicable

REFERENCE TO MICROFICHE APPENDIX

Not Applicable

BACKGROUND OF THE INVENTION

Long-term potentiation (LTP) and long-term depression (LTD) are well-studied phenomena that may be related to learning and memory. Glutamate is the main excitatory neurotransmitter in the brain. There are at least two types of glutamate receptors, the AMPA (alpha-amino-3-hydroxy-5-methylisoxazole-4-propionic acid) receptor, and the NMDA (N-methyl-D-aspartate) receptor. The mechanism by which LTP is induced does not involve AMPA receptors, but the synaptic response of potentiation results largely due to AMPA receptor activity, as described in a book by Thompson R. F., titled *"Brain: A Neuroscience Primer"*, 3rd Edition, published in New York: Worth Publishers, 2000, p. 102-117. The critical event for LTP development occurs when the cell membrane containing the NMDA channels is depolarized sufficiently, $Mg^{2+}$ leaves the channels and glutamate activation of the NMDA receptors opens the channels, allowing $Ca^{2+}$ to rush into the neuron. But if LTP involves increased transmitter release from the presynaptic terminals, how could this be caused by activation of NMDA receptors in the postsynaptic membrane? It is only possible if some chemical is released postsynaptically and diffuses back across the synaptic cleft to act on the presynaptic terminals. Some have proposed two candidate substances, which are, nitric oxide and arachadonic acid, as described in a book by Thompson R. F., titled *"Brain: A Neuroscience Primer"*, 3rd Edition, published in New York: Worth Publishers, 2000, p. 102-117.

Until recently, the role of nitric oxide and cyclic guanidine monophosphate (cGMP), (NO)/cGMP signaling in LTP has remained a matter of debate. Within the cascade, the NO receptor guanylyl cyclase (GC), the cGMP-forming enzyme that is stimulated by NO, plays a key role. Two isoforms of GC (alpha2-GC, alpha1-GC) exist. In a study described by Haghikia A., Mergia E., Friebe A., Eysel U. T., Koesling D., Mittmann T., titled *"Long-term potentiation in the visual cortex requires both nitric oxide receptor guanylyl cyclases"*, published in Journal of Neuroscience, 2007; 27: 818-823, the contribution of G isoforms to synaptic plasticity was analyzed in knock-out mice lacking either one of the GC isoforms. It was found that LTP induced in the visual cortex is NO dependent in the wild-type mice, absent in either of the GC isoform-deficient mice, and restored with application of a cGMP analog in both strains. The requirement of both NO receptor GCs for LTP, indicates the existence of two distinct NO/cGMP-mediated pathways, which have to work in concert for expression of LTP.

LTP may be present in the cortical regions of the cortico-subcortical neural network involving structures of the dorsal striatum, accumbens, and prefrontal cortex following stimulation of fornix-fimbria bundle, as described in an article by Boeijinga P. H., Mulder A. B., Pennertz C. M., Manshaden I., and Lopes Da Silva F. H., titled *"Responses of the nucleus accumbens following fornix/fimbria stimulation in the rat. Identification and long-term potentiation of mono- and polysynaptic pathways"*, published in Neuroscience, 1993; 53: 1049-1058. Conversely, in the subcortical region, due to combined activation of other receptors such as the metabotropic receptor, there is a paradoxical long-lasting decrease in the responsiveness of the AMPA receptors to glutamate release, as described in an article by Ito M., titled *"Long-term depression"*. Annual Review of Neuroscience, 1989; 11: 85-102; as well as in a book by Thompson, R. F., titled *"Brain: A Neuroscience Primer"*, 3rd Edition, published in New York: Worth Publishers, 2000, p. 102-117.

Neurons and synapses in the mammalian brain exhibit plastic changes, which occur not only during development and under physiological conditions, but also under pathological conditions. Until recently, LTP has only been directly demonstrated in humans in isolated cortical tissue obtained from patients undergoing surgery, where it displays properties identical to those seen in non-human preparations. Inquiry into the functional significance of LTP has been hindered by the absence of a model in the intact human brain. Recently, it was demonstrated that the rapid repetitive presentation of a visual checkerboard (a photic 'tetanus') leads to a persistent enhancement of one of the early components of the visual evoked potential in normal humans, as described in an article by Teyler T. J., Hamm J. P., Clapp W. C., Johnson B. W., Corballis M. C., and Kirk I. J., titled *"Long-term potentiation of human visual evoked responses."*, published in European Journal of Neuroscience, 2005; 21: 2045-2050. The potentiated response is largest in the hemisphere contralateral to the tetanized visual hemifield and is limited to one component of the visual evoked response (the N1b). This selective potentiation of only the N1b component is not related to overall brain excitability changes, but suggests that the effect is due instead to an LTP process. While LTP is known to exist in the human brain, the ability to elicit LTP from non-surgical patients will provide a human model system allowing the detailed examination of synaptic plasticity in normal subjects and may have future clinical applications in the assessment of cognitive disorders. It had been shown in a work previously described by Clapp W. C., Muthukumaraswamy S. D., Hamm J. P., Teyler T. J., and Kirk I. J., titled *"Long-term enhanced desynchronization of the alpha rhythm following tetanic stimulation of human visual cortex"*, published in Neuroscience Letters, 2006; 398: 220-223, that a photic tetanus induces LTP-like changes in the visual cortex, as indexed by enhanced event-related desynchronization (ERD) of the alpha rhythm lasting one hour, over occipital electrodes. Because ERD of the alpha rhythm is thought to represent active cortex, these results suggest that the visual tetanus induces long-lasting cortical changes, with stronger neuronal assemblies and increased neuronal output.

There has been a quest for a simple non-invasive model to induce and study LTP and LTD processes in the intact human brain. Little did anyone expect that the head-down bed rest model in conjunction with transcranial Doppler ultrasonography could provide a potential method for the non-invasive induction and recording of LTP and LTD processes. The first attempt to study the effects of head-down bed rest during motor function was described by Njemanze P. C., titled *"Cerebral lateralization for motor tasks in simulated microgravity. A transcranial Doppler technique for astronauts."* Journal of Gravitational Physiology, 2002; 9:33-34, and showed that motor function evoked changes in cerebral blood flow velocity that varied in lateralization during head-down bed rest. Further studies revealed that there may be a significant gender-related cerebral asymmetry in response to facial processing during head-down bed rest, as described by Njemanze P. C. titled *"Asymmetry in cerebral blood flow velocity with processing of facial images during head-down rest"*, published in Aviation Space and Environmental Medicine, 2004; 75:800-805. This study demonstrated unexpected results that showed in men, there was a baseline blood flow lateralization to the right hemisphere, but after 6 hours of head-down bed rest, there was a left lateralization, and after 24 hours of head down bed rest, there remained a left lateralization, and then, a tendency towards right lateralization at one hour in the post head-down bed rest period. In the converse, in women, there was a left lateralization at baseline, then a right lateralization after 6 hours of head-down bed rest. And at 24 hours, there was left lateralization, with a tendency towards no lateralization at one hour in the post head-down bed rest period. However, the latter work as well as other works published in literature, did not clarify if the gender-related response was only restricted to the facial stimuli or was a matter functional asymmetry related to brain processes in general. Particularly, in view of the fact that in another study described by Njemanze P. C., titled "*Cerebral lateralization and general intelligence: Gender-differences in a transcranial Doppler study*." Brain and Language, 2005; 92:234-239, it was demonstrated that there was a gender-related cerebral lateralization of general intelligence with right hemisphere asymmetry for general intelligence in men, and left hemisphere asymmetry in women. Further studies were undertaken, which involved color processing in men alone as described by Njemanze P. C., titled "*A symmetry of cerebral blood flow velocity response to color processing and hemodynamic changes during −6 degrees 24-hour head-down bed rest in men*." Journal of Gravitational Physiology, 2005; 12(2):33-41. This study demonstrated a right lateralization during color stimulation in men. However, the role of the effects of head-down bed rest remained unclear. Particularly, could head-down bed rest induce long-term potentiation and long-term depression during cognitive brain processes?

The technical and theoretical limitations of the conventional transcranial Doppler ultrasonography did not allow the study of brain processes that could be attributed to LTP or LTD. However, until prior art by Njemanze (US 2004/0158155) disclosed a non-invasive method to determine cerebral blood flow velocity in response to assessment tasks of a human subject, including steps of obtaining a subject's cerebral blood flow velocity in cerebral arteries on both sides of the brain using a microcomputer integrated with a transcranial Doppler ultrasound instrument with two probes placed on the temples and sample volumes focused on cerebral vessels on both sides and calculating laterality index for both arteries. Simultaneously, testing the subject with visual processing tasks presented on the screen of a digital computer while monitoring the mean blood flow velocity during each stage of the task in real-time. Njemanze '155 further discloses processing of the acquired data to determine the spectrum analysis using a microcomputer that is operatively connected to a computer workstation for image retrieval and cross-matching. The method could be used to assess human cognition like memory and learning, which have been associated with long-term potentiation and long-term depression but not demonstrating the induction and recording of LTP and LTD. The process of acquiring data includes first, presenting stimuli (i.e. task) to the subject in intervals of 60 seconds. However, Njemanze '155 fails to provide a model for studying LTP and LTD based on placing the subject on a tilt bed. In addition, Njemanze '155 further fails to teach that the subject is placed head down or head-up at different time intervals as the stimuli are being presented. Although, prior art in view of Falbo (U. S. Pat. No. 6,353,949) disclosed a tilt table in order to position a patient at various angles of incline and decline as desired by the physician, it was not obvious to anyone, and there were no published data in literature that tilting a patient to head-down bed rest could be used to induce LTP and LTD in one hemisphere or the other. While Njemanze (US 2004/0158155) accomplished the development of functional transcranial Doppler spectroscopy (fTCDS) by processing the mean cerebral blood flow velocity data using Fourier time series analysis, the methodology for combined use of fTCDS and head-down bed rest for induction and recording of LTP and LTD was not accomplished. Njemanze '155 teaches that the spectral densities are calculated and plotted from the data of all paradigms/stimuli and the peaks are identified in order to characterize fundamental vascular changes. The cortical (C) or memory peak (M) and sub-cortical peak (S) are identified. The C-peak and S-peak characterize cortical and sub-cortical processes, respectively. However, Njemanze '155 fails to establish a clear method of registering LTP and LTD, namely that the accentuation of the C-peak above baseline values represented processes of cortical long-term potentiation (CLTP), and comparison of recordings at different time intervals, conversely, the attenuation of the C-peak compared to baseline represented cortical long-term depression (CLTD). Similarly, the accentuation of the S-peak above baseline values represented processes of subcortical long-term potentiation (SLTP), and comparison of recordings at different time intervals, conversely, the attenuation of the S-peak compared to baseline represented subcortical long-term depression (SLTD). These findings became evident only after further experimentation described by Njemanze P. C. titled "*Asymmetric neuroplasticity of color processing during head down rest: a functional transcranial Doppler spectroscopy study*." Journal of Gravitational Physiology, 2008 15(2): 49-59. This work clearly showed that during head-down bed rest, in the right hemisphere but not left, in men, there was simultaneous CLTP and SLTD, wavelength-differencing was absent, but wavelength-encoding was used as cues. There were double luminance effect detectors leading to sensory conflicts. Post head-down bed rest showed reversed wavelength-differencing in both hemispheres, dual luminance effect detectors, CLTP and SLTD. The latter work resolved many of the puzzling issues surrounding experiences of astronauts of light flashes during dark adaptation in Space and proved that fTCDS may be useful in the study of the effects of neuroplasticity of simultaneous color contrast and color constancy in microgravity or simulated microgravity using the head-down bed rest model. The demonstration of the criticality of applying fTCDS to study LTP and LTD processes during head-down bed rest and then head-up bed rest, was a ground-breaking finding, that was totally unexpected but with sound theoretical rationale in hindsight. The rationale is based on the fact that, both vascular and neuronal systems of the brain have identical frequency characteristics, if not, a frequency mismatch would cause gross abnormalities. Therefore, the measurement of the vascular frequency characteristics using Fourier time series analysis would also characterize the frequency responsiveness of the neuronal system, which is otherwise expressed as LTP and LTD processes. Njemanze P. C. in the work titled "*Asymmetric neuroplasticity of color processing during head down rest: a functional transcranial Doppler spectroscopy study*." Journal of Gravitational Physiology, 15(2):49-59, 2008, proposed that HDR would elicit a novel sensory or environmental response, and has been associated with NO release from postganglionic nitrergic nerves originating from ipsilateral pterygopalatine ganglion, that innervate the arteries of the circle of Willis as has been described in animal studies by Lee, T. J. *Sympathetic modulation of nitrergic neurogenic vasodilation in cerebral arteries*. Japanese Journal of Pharmacology, 2002; 88: 26-31 and in another animal study by Okamura, T. K., H. Ayajiki, K. Fujioka, K. Shinozaki, and Toda N. *Neurogenic cerebral vasodilation mediated by nitric oxide*. Japanese Journal of Pharmacology, 2002: 88: 32-38. This unexpected non-invasive induction of LTP and LTD processes using head-down bed rest model combined with new capabilities of using fTCDS for LTP and LTD detection which was actualized in the present invention was a ground-breaking milestone that were not evident in literature and was not existent in prior art including Njemanze '155, Njemanze '979 and Crutchfield et al. (US 2002/0062078). The improved knowledge resulted from significant new experimentations that advanced the knowledge beyond the possibilities of what was known until March 2007, when the present invention was made. Now, armed with the technology to study non-invasively in an intact human being, the LTP and LTD processes, it became possible to explore other applications.

The use of the present invention to provide a model for the study of LTP and LTD has a wide range of applications for disease diagnosis, therapeutic drug management, research and rehabilitation. One object of the present invention is its application for the study of the effects of drugs of addiction and their remedies. There is accruing evidence to suggest that plasticity-related neuroadaptations within the ventral striatum and related circuitry may depend on glutamate-dopamine interactions. These neuroadaptational changes are concomitants of reinforcement learning, that may underlie drug addiction, as described in an article, in a book by Kelley, A. E., titled "*Functional specificity of ventral striatal compartments in appetitive behaviors*". In: *Advancing from the Ventral Striatum to the Extended Amygdala*. Ed: J. F. McGinty, published in New York: Annals of the New York Academy of Sciences, 1999; 877: 71-90.

Another object of the present invention is to apply the model for study of mechanisms that block LTP processes in sensory chronic pain management and disease conditions of memory deficits. It has been postulated that, activity-dependent changes in synaptic strength may contribute to the formation of memory and the expression of persistent inflammatory pain. Recently, the anterior cingulate cortex (ACC) has been proposed to play an important role for learning, memory and chronic pain. For example, it has been demonstrated that clonidine, a specific alpha2-adrenergic receptor agonist, found to be effective for the treatment of neuropathic pain, may exert analgesic effect by depressing the synaptic plasticity in spinal dorsal horn, via activation of muscarinic receptor-NO-cGMP pathway, as described in an article by Ge Y. X., Xin W. J., Hu N. W., Zhang T., Xu J. T., and Liu X. G., titled "*Clonidine depresses LTP of C-fiber evoked field potentials in spinal dorsal horn via NO-cGMP pathway*", published in Brain Research, 2006; 1118: 58-65. The benzodiazepine-diazepam impairs memory and LTP formation in the hippocampus and depresses spinal plasticity related-changes produced by noxious stimulation via activation of the gamma aminobutyric acid GABA(A)-benzodiazepine receptor complex as described in an article by Hu X. D., Ge Y. X., Hu N. W., Zhang H. M., Zhou L. J., Zhang T., Li W. M., Han Y. F., Liu X. G., titled "*Diazepam inhibits the induction and maintenance of LTP of C-fiber evoked field potentials in spinal dorsal horn of rats*" published in Neuropharmacology, 2006; 50: 238-244.

A further object of the present invention is its application to processes mediated by other GABA-ergic neurons, such as in adaptive eating disorders. The phasic glutamate release could reverse the hyperpolarization of the medium spiny neurons induced by GABA, resulting in a major switch in behavioral patterning for feeding, as described in an article in a book by Kelley, A. E., titled "*Functional specificity of ventral striatal compartments in appetitive behaviors*". In: *Advancing from the Ventral Striatum to the Extended Amygdala*. Ed: J. F. McGinty, published in New York: Annals of the New York Academy of Sciences, 1999; 877: 71-90.

Another object of the present invention is its application for understanding of processes mediated by GABA-ergic neurons, such as those involved in color processing. The phasic glutamate release could reverse the hyperpolarization of the medium spiny neurons induced by GABA, resulting in interference with opponent color processing as described in an article by Njemanze, P. C. titled "*Asymmetry of cerebral blood flow velocity response to color processing and hemodynamic changes during −6 degrees 24-hour head-down bed rest in men*", published in Journal of Gravitational Physiology, 2005; 12: 33-41.

Another object of the present invention is its application for understanding of processes mediated by glutamate-dopamine interaction in motor and limbic functions, as described in an article in a book by Healy D. J. and Meador-Woodruff J. H., titled "*Glutamatergic modulation of subcortical motor and limbic circuits*". In: *Advancing from the Ventral Striatum to the Extended Amygdala*. Ed: J. F. McGinty, published in New York: Annals of the New York Academy of Sciences, 1999; 877: 684-687.

Another object of the present invention is the activation of ipsilateral glutamate and NO release using the head-down bed rest (HDR) maneuver. HDR is used for simulation of the cardiovascular effects during Space flights. It has been suggested that HDR exposure results in imbalance between sympathetic vasoconstrictor traffic and vasodilator effects of NO release as described in an article by Kamiya A., Iwase S., Michikami D., Fu Q., Mano T., Kitaichi K., and Takagi K., titled "*Increased vasomotor sympathetic nerve activity and decreased plasma nitric oxide release after head-down bed rest in humans: disappearance of correlation between vasoconstrictor and vasodilator*" published in Neuroscience Letters, 2000; 281: 21-24, and altered cerebral mean flow velocity (MFV) as described in an article by Njemanze, P. C. titled "*Asymmetry of cerebral blood flow velocity response to color processing and hemodynamic changes during −6 degrees 24-hour head-down bed rest in men*", published in Journal of Gravitational Physiology 2005; 12: 33-41. This would suggest that HDR elicited a novel sensory or environmental response and has been associated with NO release from postganglionic nitrergic nerves originating from ipsilateral pterygopalatine ganglion, as described in articles by Lee, T. J., titled "*Sympathetic modulation of nitrergic neurogenic vasodilation in cerebral arteries*", published in Japanese Journal of Pharmacology, 2002; 88: 26-31; and by Okamura, T. K., H. Ayajiki, K. Fujioka, K. Shinozaki, and Toda N., titled "*Neurogenic cerebral vasodilation mediated by nitric oxide*", published in Japanese Journal of Pharmacology 2002:88:32-38. It is plausible that, the NO released diffuses back across the synaptic cleft to act on presynaptic terminals, to cause increased release of glutamate, as described in a book by Thompson, R. F., titled "*Brain: A Neuroscience Primer*", 3rd Edition, published in New York: Worth Publishers, 2000, p. 102-117. The changes in MFV induced by HDR suggest a left lateralization but relative right hypoperfusion. Therefore, the expected phasic glutamate release that overcomes GABA-mediated cortical inhibition leading to sustained ipsilateral LTP processes would occur in the cortical regions of the right hemisphere.

Another object of the present invention is to assess the state of brain autoregulation during unconsciousness. Autoregulation refers to the capability of the cerebrovascular system to maintain normal cerebral perfusion despite fluctuation in arterial blood pressure. Failure of brain autoregulation results in unconsciousness with fall in arterial blood pressure. HDR induced during normal function of brain autoregulation results in cerebral hypoperfusion as described in an article by Njemanze, P. C. titled "*Asymmetry of cerebral blood flow velocity response to color processing and hemodynamic changes during −6 degrees 24-hour head-down bed rest in men*", published in Journal of Gravitational Physiology, 2005; 12: 33-41. However, HDR is a well known maneuver for inducing brain reperfusion during unconsciousness, in a failed state of autoregulation. It is the object of the present invention to determine at which point there is restoration of normal brain perfusion that sustains cortical LTP and subcortical LTD.

A further object of the present invention is to provide a method that analyzes MFV data obtained in real-time by Fourier algorithm. The obtained spectral density estimates are plotted to determine the peaks for cortical and subcortical responses using an algorithm called functional transcranial Doppler spectroscopy (fTCDS) as described in an article by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49.

SUMMARY OF THE INVENTION

The present invention provides a method for monitoring LTP and LTD, comprising placing a subject in HDR position and monitoring real-time MFV of the subject during psychophysiologic tasks comprising sensory, adaptive, visual, auditory or motor. The effects of different interventions on LTP and LTD could be evaluated. The special embodiment of this invention, illustrated in the specifications, includes block and schematic diagrams for the format of the instrumentation, and how the system operates, by way of example. The subject refers to an intact brain of a human or primate under testing, by way of example. The system comprises a tilt bed for performing the HDR, a bilateral simultaneous transcranial Doppler (TCD) ultrasound device, and a head-gear with fitted two 2 MHz probes. The TCD probes are placed on the acoustic window on the temporal bones above the zygomatic arc, on both sides of the head and focused on major cerebral vessels such as the right and left middle cerebral artery (RMCA and LMCA), respectively, by way of example. The TCD device could be modified for use in primates. The psychophysiologic stimulation could be colors such as that described in detail in U. S. patent application Ser. No. 11/636, 554 by Njemanze P. C. Other means of psychophysiologic stimulation could be used such as facial processing as described by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. It also includes use of psychomotor tasks such as simple finger movements as described in an article by Njemanze, P. C., titled "*Cerebral lateralization for motor tasks in simulated microgravity. A transcranial Doppler technique for astronauts*", Journal of Gravitational Physiology, 2002; 9:33-34. The MFV is recorded, and then analyzed using Fourier analysis to derive spectral density estimates that shows cortical and subcortical peaks as described in an article by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49.

These and other objects of the present invention may become apparent to those skilled in the art upon reviewing the description of the invention as set forth hereinafter, in view of its drawings.

DETAILED DESCRIPTION OF THE INVENTION

Figure 1:
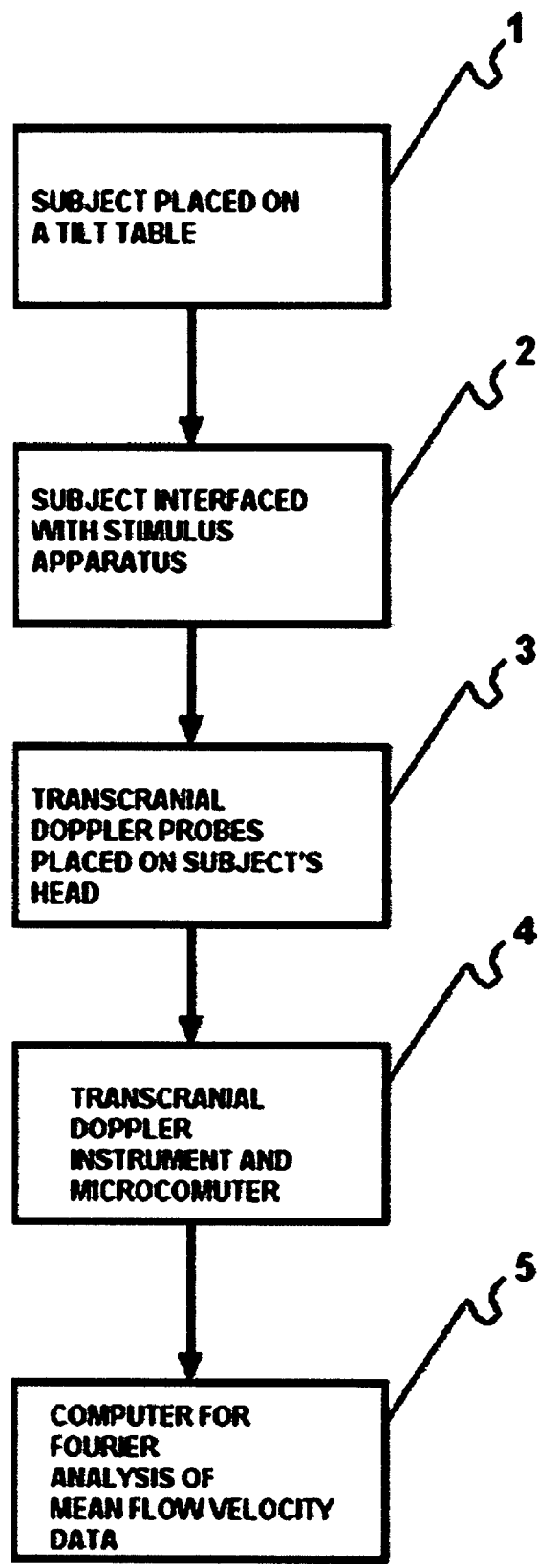
FIG. 1 shows the schematic diagram of the present invention.

The block diagram of the present invention is illustrated in FIG. 1. As shown therein, the subject is placed on a tilt bed 1. A number of devices could be modified to provide the required head up-tilt (HUT) at 30 degrees or HDR at −6 degrees. For example, a Backswing exerciser (Backtrack Div. Pasadena Calif.) could be modified as tilt bed. The subject is interfaced with a stimulus apparatus 2. Two 2 MHz transcranial Doppler probes of a transcranial Doppler device, that could be obtained from a company called DWL, Sipplingen, Germany, by way of example, are fitted on a head gear placed on the temporal bones 3, with ultrasound sample volumes focused in the main stem of major cerebral vessels, such as the RMCA and LMCA, respectively, by way of example. The real-time MFV measured by the TCD instrument and microcomputer 4, could be stored on the same or a separate PC 5 for statistical analyses including Fourier time series.

Figure 2:
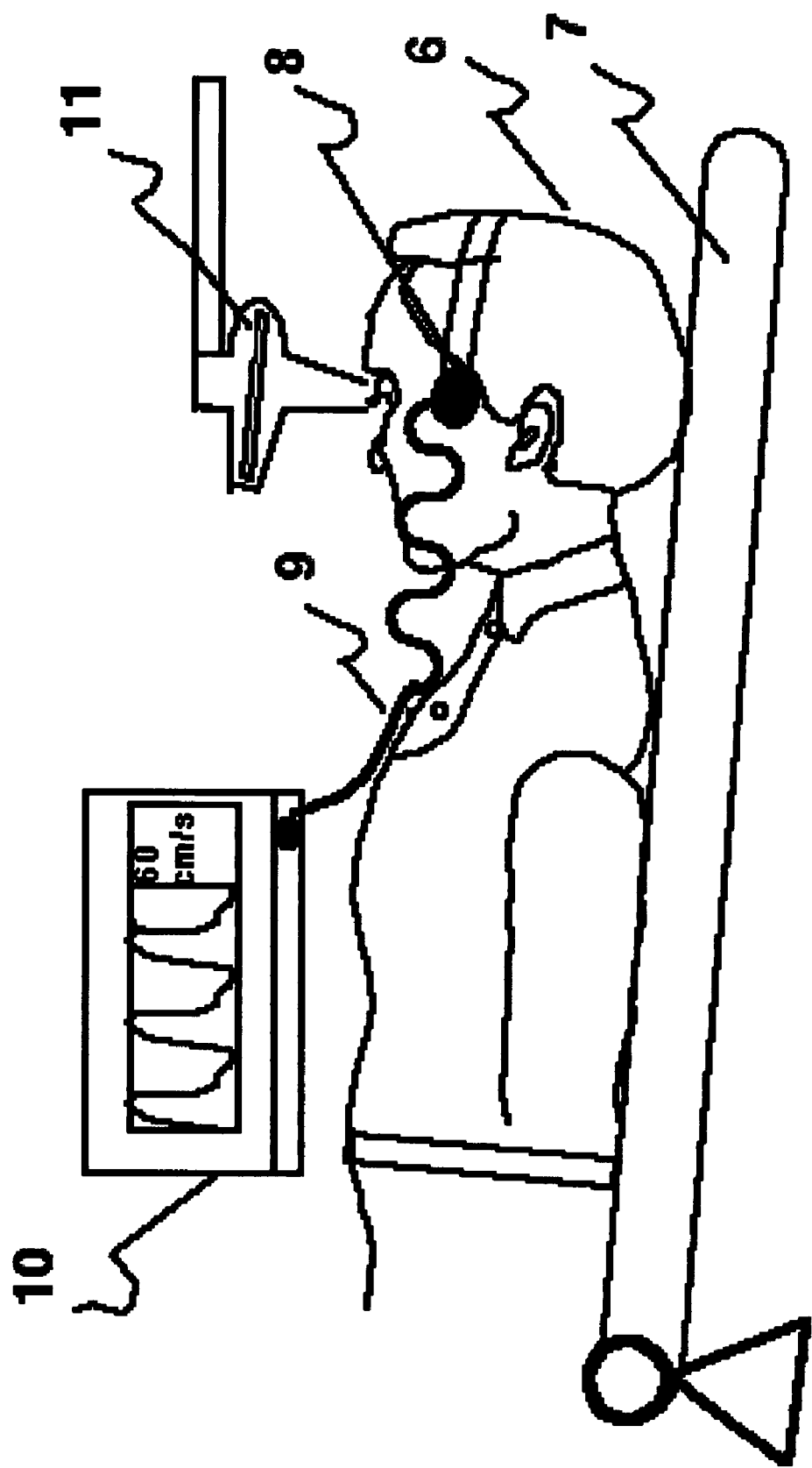
FIG. 2 shows a subject setup with the present invention.

FIG. 2 shows a subject setup with the present invention. The subject 6 is placed on the tilt bed 7. The TCD probe on the left 8 and right (not shown) sides are placed on the temporal bones bilaterally, and connected to the TCD device by an electrical cord 9. The TCD device 10 has a monitor display of the MFV trends recorded. The stimulus administration device 11 could be that for colors as described in an article by Njemanze P. C. titled "*Asymmetry of cerebral blood flow velocity response to color processing and hemodynamic changes during −6 degrees 24-hour head-down bed rest in men*", published in Journal of Gravitational Physiology, 2005; 12: 33-41, by way of example.

Figure 3:
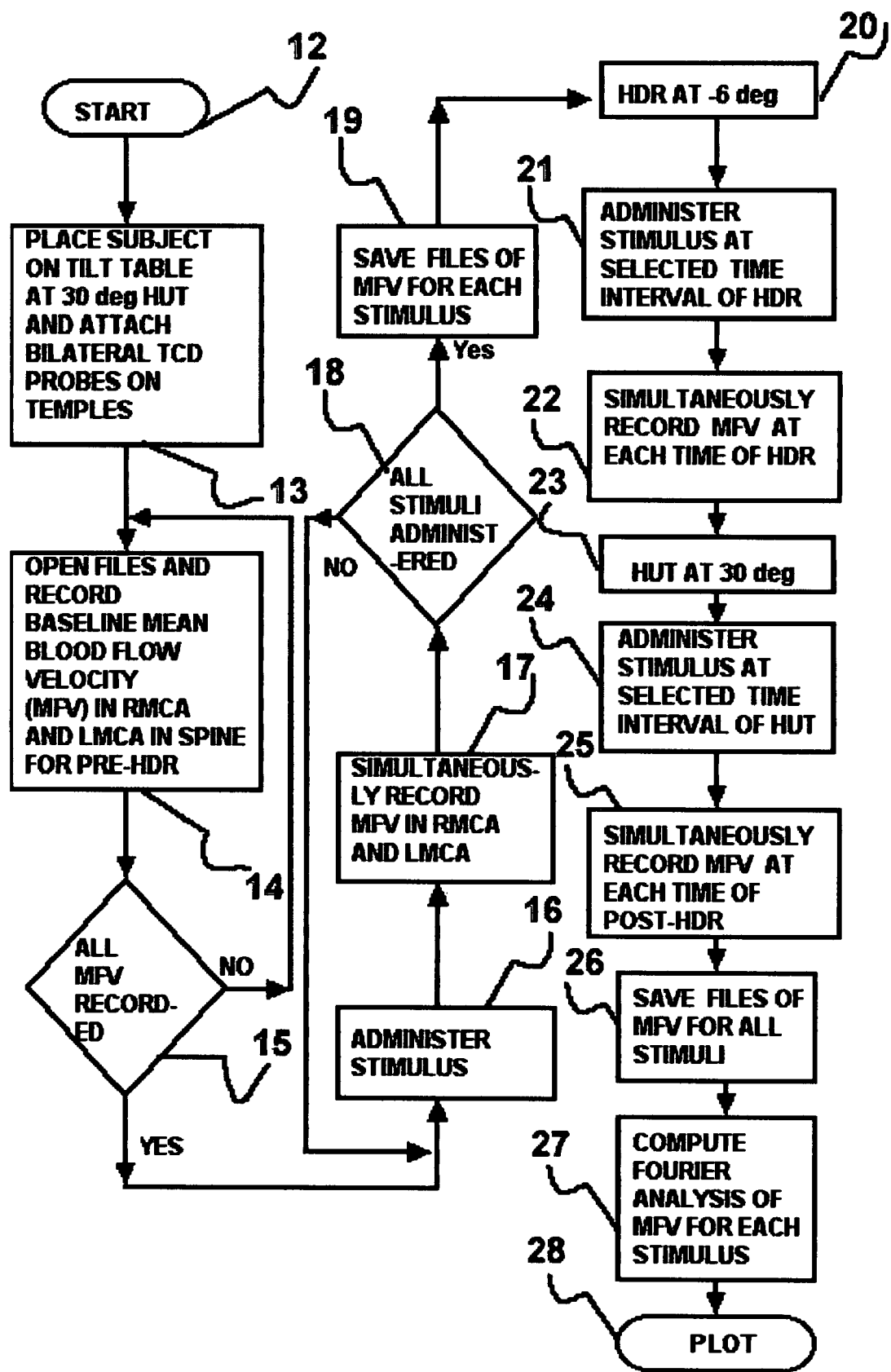
FIG. 3 shows the program flow chart of the invention.

FIG. 3 shows the functional flow chart of the present invention by way of example. The procedure begins 12 with the subject placed supine on a tilt bed with 30 degrees HUT. The angle for HUT and HDR, could be varied according to the peculiar requirements of the experimental procedure, 30 degrees HUT and −6 degrees HDR were chosen here, by way of example. A duration of 24 hours of HDR (24H-HDR) was also selected by way of example, shorter or longer duration of HDR could be necessary if required. Two 2 MHz probes of an operational fTCD device are attached on both temples above the zygomatic arc 13. The files are opened in the microcomputer of the fTCD and labeled baseline, for MFV in the RMCA and LMCA, respectively. All files and recordings of baseline MFV data are completed, if not 15, further recordings are done. Stimulus administration 16, for example, color stimulation (Black, Blue, White, Yellow, and Red) could be carried out as described in an article by Njemanze P. C. titled "*Asymmetry of cerebral blood flow velocity response to color processing and hemodynamic changes during −6 degrees 24-hour head-down bed rest in men*", published in Journal of Gravitational Physiology, 2005; 12: 33-41. Simultaneously, real-time MFV in the RMCA and LMCA are recorded and labeled for each stimulus 17, and labeled Pre-HDR. All stimulations must be completed and recorded, if not, further stimulation and recording are done 18. All files of MFV trends are saved and labeled for each stimulus 19. The patient is tilted head-down to −6 degrees 20. The stimuli are administered at selected time intervals for a given duration 21, for example 6H-HDR, and 24H-HDR for 60 seconds each. At each time, MFV is recorded during stimulation and marked for the particular time interval 22. The subject is then tilted head up again to 30 degrees for Post-HDR recording 23. Stimuli are administered at the selected time interval of HUT 24. Duration of one hour after HDR was chosen for Post-HDR recording, by way of example. All real-time MFV data are simultaneously recorded with stimulation for each selected time interval in Post-HDR 25. All files of MFV data are labeled and saved for each stimulus at each selected time interval 26. The data could be processed on the same computer of the fTCD device, or transferred for statistical analysis including Fourier time series analysis 27 and plotted for each stimulus 28 as described in an article by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. The same protocol could be repeated in test subjects after a drug or other interventions, to evaluate the drug-related effects.

FIG. 4A shows the plot of spectral density estimates, overlaid for each color stimulus, for the Pre-HDR RMCA recording, with peaks designated as C-peaks 29 for cortical responses, and S-peaks 30 for subcortical processes, as described in detail in an article by Njemanze, P. C., titled "*Cerebral lateralization for facial processing: Gender-related cognitive styles determined using Fourier analysis of mean cerebral blood flow velocity in the middle cerebral arteries*", published in Laterality, 2007; 12: 31-49.

FIG. 4B shows the F-peaks 31, C-peaks 32, and S-peaks 33 in the RMCA at 6H-HDR, for each stimulus, overlaid. The F-peaks 31 relates to reflections from the extremities and is irrelevant the present analysis. After six hours of HDR, there is accentuation of C-peaks 32, suggestive of cortical long-term potentiation (CLTP). On the other hand, there is attenuation of S-peaks 33 at 6H-HDR, or subcortical long-term depression (SLTD).

FIG. 4C shows the F-peaks 34, C-peaks 35 and S-peaks 36 in the RMCA at 24H-HDR, for each stimulus, overlaid. The CLTP and SLTD evoked by the stimuli were maintained at levels similar to that at 6H-HDR.

FIG. 4D shows the C-peaks 37 and S-peaks 38 in the RMCA at Post-HDR, for each stimulus, overlaid. The CLTP and SLTD evoked by the stimuli were maintained at levels similar to that at 6H-HDR.

FIG. 5A shows the F-peaks 39, C-peaks 40, and S-peaks 41 in the LMCA at Pre-HDR, for each stimulus, overlaid.

FIG. 5B shows the F-peaks 42, C-peaks 43, and S-peaks 44 in the LMCA at 6H-HDR, for each stimulus, overlaid. In contrast, to the peaks at 6H-HDR in the RMCA (FIG. 4B), there were no CLTP and SLTD.

FIG. 5C shows the F-peaks 45, C-peaks 46, and S-peaks 47 in the LMCA at 24H-HDR, for each stimulus, overlaid. Compared to the peaks in the RMCA (FIG. 4C), CLTP and SLTD were absent.

FIG. 5D shows the F-peaks 48, C-peaks 49 and S-peaks 50 in the LMCA at Post-HDR, for each stimulus, overlaid. Compared to peaks in the RMCA (FIG. 4D), CLTP and SLTD were absent.

A detailed description of an experiment to determine ipsilateral right hemisphere CLTP and SLTD, during color processing, by way of example, is set forth below.

Materials and Methods

The study included 8 men of mean±SD age of 24.8±2.5 years, all were right handed as determined using a hand preference questionnaire, as described in an article by Peters, M., titled "*Description and validation of a flexible and broadly usable hand preference questionnaire*" published in Laterality, 1998; 3: 77-96. Visual acuity, color vision and color recognition were normal, as described in a book by Frisén L., titled "*Clinical Tests of Vision*" published in New York: Raven Press, 1990. All had normal findings for cardiovascular, neurologic and respiratory systems, and maintained the usual restrictions for cognitive studies, as described in an article by Stroobant, N., and Vingerhoets G., titled "*Transcranial Doppler ultrasonography monitoring of cerebral hemodynamics during performance of cognitive tasks. A review*" published in Neuropsychological Review, 2000; 10: 213-231.

All subjects signed written informed consent according to the Declaration of Helsinki, and the Institutional Review Board approved the study protocol. The TCD scanning procedure was similar to that used in other cognitive studies, described elsewhere, in an article by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. Briefly, TCD studies were performed using two 2 MHz probes of a bilateral simultaneous TCD instrument (Multi-Dop T, DWL, Singen, Germany), with sample volume placed in the RMCA and LMCA main stems, at a depth of 50 mm. Pre-HDR recordings were made with the subject lying supine, with head and trunk elevated at 30 degrees. The subject was placed on a bed, positioned with head-down angle set at −6 degrees. Subjects consumed regular light meals, as prescribed by a dietician, and a bedpan was used for toileting. After duration of 24 hours of bed rest, subjects were returned to conditions similar to Pre-HDR, with head and trunk elevated at 30 degrees, and Post-HDR recording began after 60 minutes of rest.

Tasks

The tasks were designed by the inventor, and have demonstrated consistency and reliability with TCD ultrasonography in studies in our laboratory. The detailed design and rationale have been described elsewhere, in an article by Njemanze P. C. titled "*Asymmetry of cerebral blood flow velocity response to color processing and hemodynamic changes during −6 degrees 24-hour head-down bed rest in men*", published in Journal of Gravitational Physiology, 2005; 12: 33-41. Briefly, specially adapted 3D-viewing device (Viewmaster, Portland, Oreg.) was painted inside with black paint, and the aperture closed to light for Black and opened to direct view of light source for White. The right aperture of the device was covered, but the left aperture was open, to be backlit from reflection, from a remotely placed light source. The light source was a tungsten coil filament, of a general service lamp ran at a constant 24V and 200 W, with a color temperature of about 2980 K and approximately 20 lumens/watt. The light was projected onto a white flat screen, placed 125 cm from the lamp. The screen was placed 80 cm from the nose ridge of the subject. Optical homogenous filters were placed on the reel of the Viewmaster, in the light path for color stimulation. Kodak Wratten filters: Deep Blue (No. 47B) with short dominant wavelength (λ) of $S_\lambda=452.7$ nm; Deep Yellow (No. 12) with medium dominant wavelength (λ) of $M_\lambda=510.7$ nm, and Red Tricolor (No. 25) with long dominant wavelength (λ) of $L_\lambda=617.2$ nm, were used. The excitation purity and luminous transmittance are provided in the manufacturer's manual—*Kodak Photographic Filters Handbook.* Rochester, N. Y.: Eastman Kodak Company, Publication No. B-3, 1990.

For each stimulus condition, a continuous train of velocity waveform envelopes, was recorded for 60-s simultaneously, for the RMCA and LMCA, respectively. The Pre-HDR baseline condition was dark resting state, with the subject mute, still, and attention focused within the Black visual field, with no mental or manual tasks to perform. The same condition was maintained at onset of each data acquisition, in HDR and Post-HDR. The condition for data acquisition, during visual stimuli presentation, was identical to that of baseline, except for the color slides and White light.

Calculations

Artifacts of recordings were marked and removed. Velocity waveform envelopes for the relevant 60-s intervals were first averaged in 10-s segments, to produce six values for dark condition and each color condition, respectively. The MFV values were used for Fourier analysis.

Fourier Analysis fTCDS is based on Fourier transform algorithm. Single series Fourier analysis (Time series and forecasting module, Statistica for Macintosh, StatSoft, OK), was applied to a dataset of 48 data points of MFV, recorded for 60-s of stimulus duration, in eight men. The application of Fourier analysis to MFV data, to determine cognitive responses, has been described in detail elsewhere, in an article by Njemanze P. C., titled "Cerebral lateralization for facial processing: *Gender-related cognitive styles determined using Fourier analysis of mean cerebral blood flow velocity in the middle cerebral arteries*", published in Laterality, 2007; 12: 31-49. Prior work revealed that in the human cerebrovascular system there is a consistent pattern of peaks associated with cortical and ganglionic reflection sites with constant frequencies for maximum spectral density estimate (maxima) and minimum spectral density estimate (minima) relative to the number of observations, as described by Njemanze, P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. The latter was used as a guide for selection of the data processing protocol. For each artery (RMCA and LMCA, respectively) 24 data points of spectral density and their corresponding frequencies were obtained. For each stimulation, the peak regions were identified as clusters of three highest spectral densities with maxima (frequency of the maximum spectral density) at frequencies 0.125 (first harmonic), 0.25 (second harmonic) and 0.375 (third harmonic), respectively; and were compared to trough regions comprising clusters of three lowest spectral densities with minima (frequency of the lowest spectral density) at frequencies 0.0625, 0.1875, and 0.3125, respectively. A statistically significant difference at $p<0.05$ confirmed the separation of peak regions from trough regions. The origin of these peaks could be presumed, from what is known of the anatomy of the vascular system. A major proximal reflection site relative to recording site at the main stem of the MCA was shown to arise from the upper extremities—finger tips, while both hands were stretched side ways, and has been shown to disappear on complete elbow flexion, as described by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. The spectral density estimates derived from single series Fourier analysis, were plotted, and the frequency regions with the highest estimates were marked as peaks. The peak frequency region associated with fingertip reflection site (F-peak) included all spectral densities between the two minima at frequencies 0.0625 to 0.1875, with maxima at 0.125. The peak region associated with the cortical processes (C-peak) included all spectral densities between the two minima at frequencies 0.1875 to 0.3125, with maxima at 0.25. For the subcortical region (S-peak), the peak included spectral densities between the two minima at frequencies 0.3125 to 0.4375, with maxima at 0.375. The frequencies with the greatest spectral densities; that is, the frequency regions, consisting of many adjacent frequencies, that contribute most to the overall periodic behavior of the series for each vessel (RMCA and LMCA, respectively), were identified as fundamental (F-peak), cortical (C-peak) and subcortical (S-peak), peaks and were plotted as described in detail elsewhere, in an article by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. The latter peaks (C-peak and S-peak), were relevant for assessment of cortical and subcortical responses.

The site of origin of spectral density peaks could be determined, by calculating the distances from which the reflections eliciting these peaks emanate from, relative to the measurement site in the main stem of the MCA. It could be considered that the fundamental frequency designated as F-peak represents the first harmonic of the cardiovascular oscillation. The fundamental frequency f of the $1^{st}$ harmonic was determined by the mean heart rate per second for example: 74 bpm/60 seconds=1.23 Hz. In other words, the F-, C- and S-peaks occurred at multiples of the $1^{st}$ harmonic, at $2^{nd}$ and $3^{rd}$ harmonics, respectively. The F-peak could emanate from a proximal site in the lower body (or fingertips of the upper extremities with hands stretched sideways), and the distance could be estimated from the arterial pulse wave velocity (aPWV) from the carotid artery to the femoral artery. The distal reflection sites would yield peaks at the $2^{nd}$ and $3^{rd}$ harmonics, that is, at twice and thrice the frequency of the first. These reflections could have arisen from distal cortical and ganglionic (subcortical) terminal arteries, respectively. The higher $4^{th}$ harmonic would yield distances too close to the measurement site that would suggest reflections from the MCA bifurcation or trifurcation. The calculated distances would be approximate estimates, and have accuracy to the extent the aPWV in the common carotid is close to that in the MCA. The distance (D), of the reflection site from measurement point, could be estimated given the frequency of the harmonic f, and the aPWV (c). The presumed reflection site is given by ($D=c/f$). Therefore, the putative reflection sites for the $1^{st}$ harmonic, would be at $D_1=\frac{1}{4}\lambda$ or c/4 f; the $2^{nd}$ harmonic, at $D_2=\frac{1}{8}\lambda$ or c/8×2f, and $3^{rd}$ harmonic, at $D_3=\frac{1}{16}\lambda$ or c/16×3f In human carotid-femoral vessels, several estimates put $c=6.15$ msec$^{-1}$, and in the common carotid artery, $c = 5.5 \pm 1.5$ msec$^{-1}$. The estimated distance may not correlate with known morphometric dimensions of the arterial tree.

Based on prior experiments by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49, for all stimulations, in both men and women, the F-, C- and S-peaks, occurred at regular frequency intervals of 0.125, 0.25 and 0.375, respectively. The latter frequencies were relative to number of observations. These frequencies could be converted to cycles per second (Hz), assuming that the fundamental frequency of cardiac oscillation was the mean heart rate as demonstrated above: 74 bpm/60 seconds=1.23 Hz. Thus, the distance of the reflection site for F-peak could be presumed to emanate from a site at $D_1 = \frac{1}{4}\lambda$ or c/4f, or 6.15 (m/s)/4*1.23 Hz=125 cm. Taking into account vascular tortuosity, the estimated distance approximates that from the measurement site in the MCA to an imaginary site of summed reflections, close to the finger tips when stretched sideways. The C-peak occurred at the 2$^{nd}$ harmonic, such that, the estimated arterial length (common carotid c=5.5 msec$^{-1}$) was given by $D_2 = \frac{1}{8}\lambda$ or c/8×2f, or 28 cm; and a frequency $f_2$ of 2.46 Hz. This length approximates the visible arterial length from the main stem of the MCA, through vascular tortuosity and around the cerebral convexity, to the end vessels at distal cortical sites such as the occipito-temporal junction on carotid angiograms of adults. The S-peak occurred at the 3$^{rd}$ harmonic, and may have arisen from an estimated site at $D_3 = \frac{1}{16}\lambda$ or c/16×3f or 9.3 cm; and a frequency $f_3$ of 3.69 Hz. The latter approximates the visible arterial length of the lenticulostriate arteries from the main stem of the MCA on carotid angiograms as described by Kang, H. S., Han, M. H., Kwon, B. J., Kwon, O. K., Kim, S. H., and Chang, K. H. titled "*Evaluation of the lenticulostriate arteries with rotational angiography and 3D reconstruction.*" American Journal of Neuroradiology, 2005, 26, 306-312.

Although not displayed, the 4$^{th}$ harmonic would be expected to arise from the MCA bifurcation in closest proximity to the measurement site in the main stem of the MCA. The pre-bifurcation length from the measurement point would be given by $D_4 = \frac{1}{32}\lambda$ or c/32×4f, or 3.5 cm; and a frequency $f_2$ of 4.92 Hz. The calculated length approximates that of the segment of MCA main stem just after the carotid bifurcation, where probably the ultrasound sample volume was placed, to the MCA bifurcation or trifurcation, as the case may be. Thus, it is plausible that these estimates approximate actual lengths. The calculated distances have important implications for understanding the timing of activations at both subcortical and cortical structures. The ratio of $D_3:D_2$ or $f_3:f_2$ was 1:3, and may also indicate the ratio of temporal activations at the cortical and subcortical sites, respectively.

Other Statistics.

All analyses were performed using the software package (Statistica, StatSoft, OK, USA). Results were given as mean±SD. Analyses of variance (ANOVA) was applied to spectral density estimates between two minima including the peak (as maxima), to examine the effects of stimulation on cortical and subcortical responses. Comparison of MFV data, under different stimulation conditions was performed using ANOVA with repeated measures, and when applicable, it was followed by a planned Schaeffé contrast. The latter examined LUMINANCE effect by comparison of Black versus White. A specific LUMINANCE effect, rather than non-specific light effect, would be expected to occur along an achromatic axis that runs in an opposite direction to chromatic axis, from dark baseline. A WAVELENGTH-encoding effect was considered present, when longer wavelength color (Yellow) elicited higher spectral density estimates than shorter wavelength color (Blue), at cortical or subcortical peaks. An ENERGY-encoding effect was considered present, when high frequency color (Blue), elicited higher spectral density estimates than low frequency color (Yellow), at cortical or subcortical peaks. A WAVELENGTH-differencing effect was considered present, when WAVELENGTH-encoding effect was present in the subcortical region, and ENERGY-encoding in the cortical region, for blue/yellow pair of colors. A reverse WAVELENGTH-differencing was considered present, when WAVELENGTH-encoding effect was present in the cortical region, and ENERGY-encoding in the subcortical region, for blue/yellow pair of colors. A luminance sensory conflict was regarded as present, when luminance effect responsiveness occurred in two separate brain regions, simultaneously. A color sensory conflict was regarded as present, when wavelength-differencing occurred in two separate brain regions, simultaneously. Cortical long-term potentiation (CLTP) was considered present, when spectral density peaks (C-peaks) were significantly accentuated over Pre-HDR amplitudes, and was higher than subcortical peaks (S-peaks). On the other hand, subcortical long-term depression (SLTD) was considered to be present, when spectral density peaks (S-peaks) were significantly attenuated under Pre-HDR amplitudes, and was lower than cortical peaks.

Results

To examine the effect of HDR on RMCA MFV, an ANOVA with repeated measures was performed, with the design structure of 4×5: four levels of data collection TIMES (Pre-HDR, 6H-HDR, 24H-HDR and Post-HDR), and five levels of STIMULATIONS (Black, Blue, White, Yellow and Red). There was a main effect of data collection TIMES, $F(3,141)=44.6$, $p<0.0001$. There was a main effect of STIMULATIONS, $F(4,188)=5.96$, $p<0.001$. There was no TIMES× STIMULATIONS interaction, (p=NS). Planned Schaeffé contrast revealed that, RMCA MFV at Pre-HDR (65.6 cm/s) was significantly higher than at 24H-HDR (59.4 cm/s; $p<0.0001$) and Post-HDR (59.7 cm/s; $p<0.0001$), but not at 6H-HDR (67.5 cm/s; p=NS). RMCA MFV for the two 'opponent colors'—Blue (63.7 cm/s; $p<0.001$) and Yellow (63.4 cm/s; $p<0.05$) were higher than Black baseline (62.3 cm/s). However, RMCA MFV for White (62.8 cm/s; p=NS) and Red (63 cm/s; p=NS) was same as baseline. Similarly, ANOVA analysis for the LMCA showed that, there was a main effect of data collection TIMES, $F(3,141)=22.8$, $p<0.0001$. There was a main effect of STIMULATIONS, $F(4,188)=7.7$, $p<0.0001$. There was no TIMES×STIMULATIONS interaction (p=NS). Planned Schaeffé contrast revealed that LMCA MFV at Pre-HDR (64.5 cm/s) was significantly higher than at 24H-HDR (59.4 cm/s; $p<0.0001$) and Post-HDR (60.2 cm/s; $p<0.0001$), but not at 6H-HDR (65.4 cm/s; p=NS).

LMCA MFV for the colors Blue (63.7 cm/s; $p<0.0001$), Yellow (62.7 cm/s; $p<0.05$) and Red (62.5 cm/s; $p<0.05$) was higher than for Black baseline (62.3 cm/s). However, LMCA MFV for White (62.2 cm/s; p=NS) was same as baseline. In comparison to Pre-HDR, at 6H-HDR, MFV showed a tendency to increase, but decreased at 24H-HDR and Post-HDR. The tendency toward hypoperfusion at 24H-HDR and Post-HDR, was more in the RMCA than LMCA. The latter creates a relative side-to-side difference from baseline that, may suggest a left lateralization.

Figure 4:
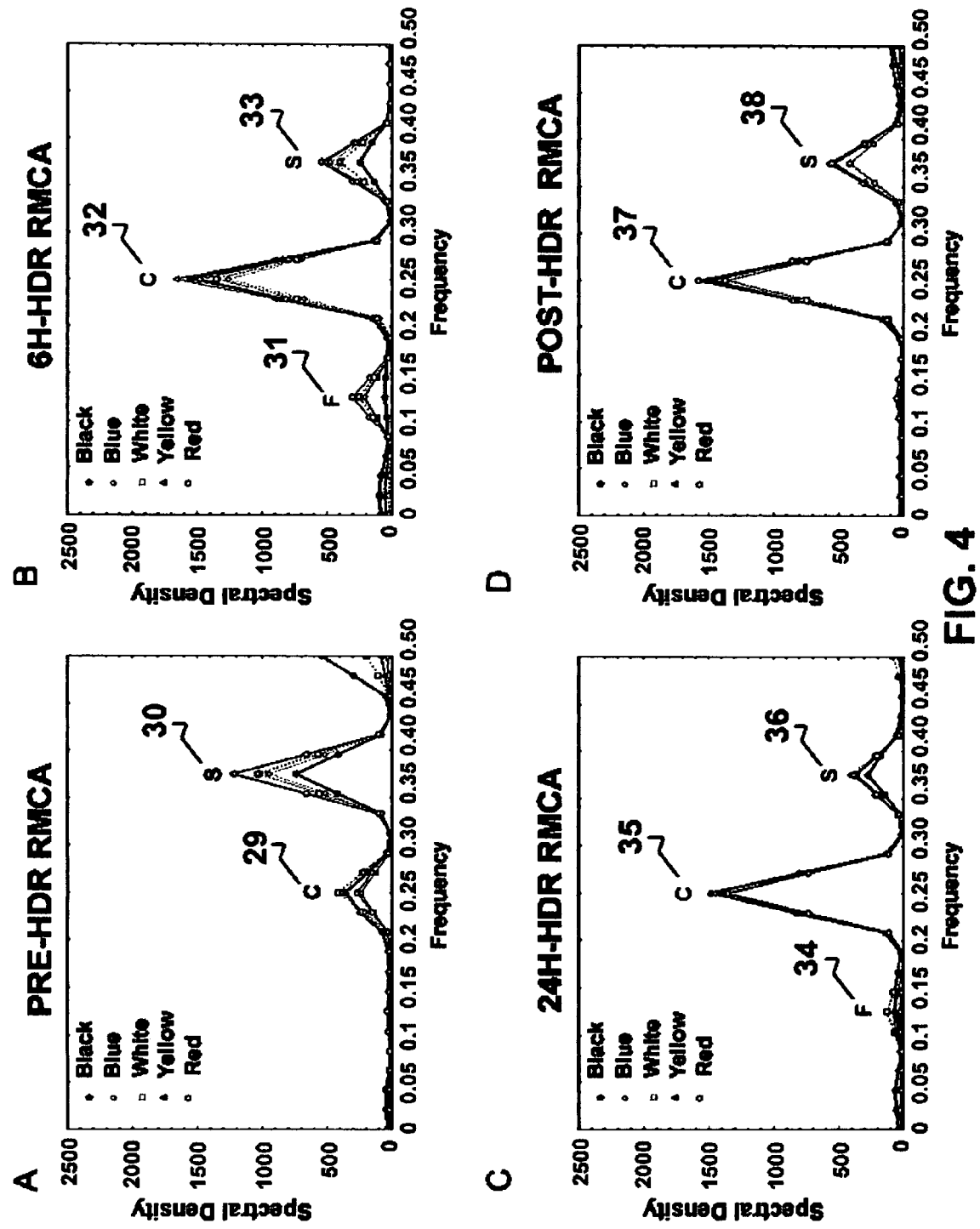
FIG. 4A shows the cortical (C-peak) and subcortical (S-peak) peaks for each color stimulation in the RMCA at Pre-HDR.
FIG. 4B shows the cortical (C-peak) and subcortical (S-peak) peaks for each color stimulation in the RMCA at 6H-HDR.
FIG. 4C shows the cortical (C-peak) and subcortical (S-peak) peaks for each color stimulation in the RMCA at 24H-HDR.
FIG. 4D shows the cortical (C-peak) and subcortical (S-peak) peaks for each color stimulation in the RMCA at Post-HDR.
Figure 5:
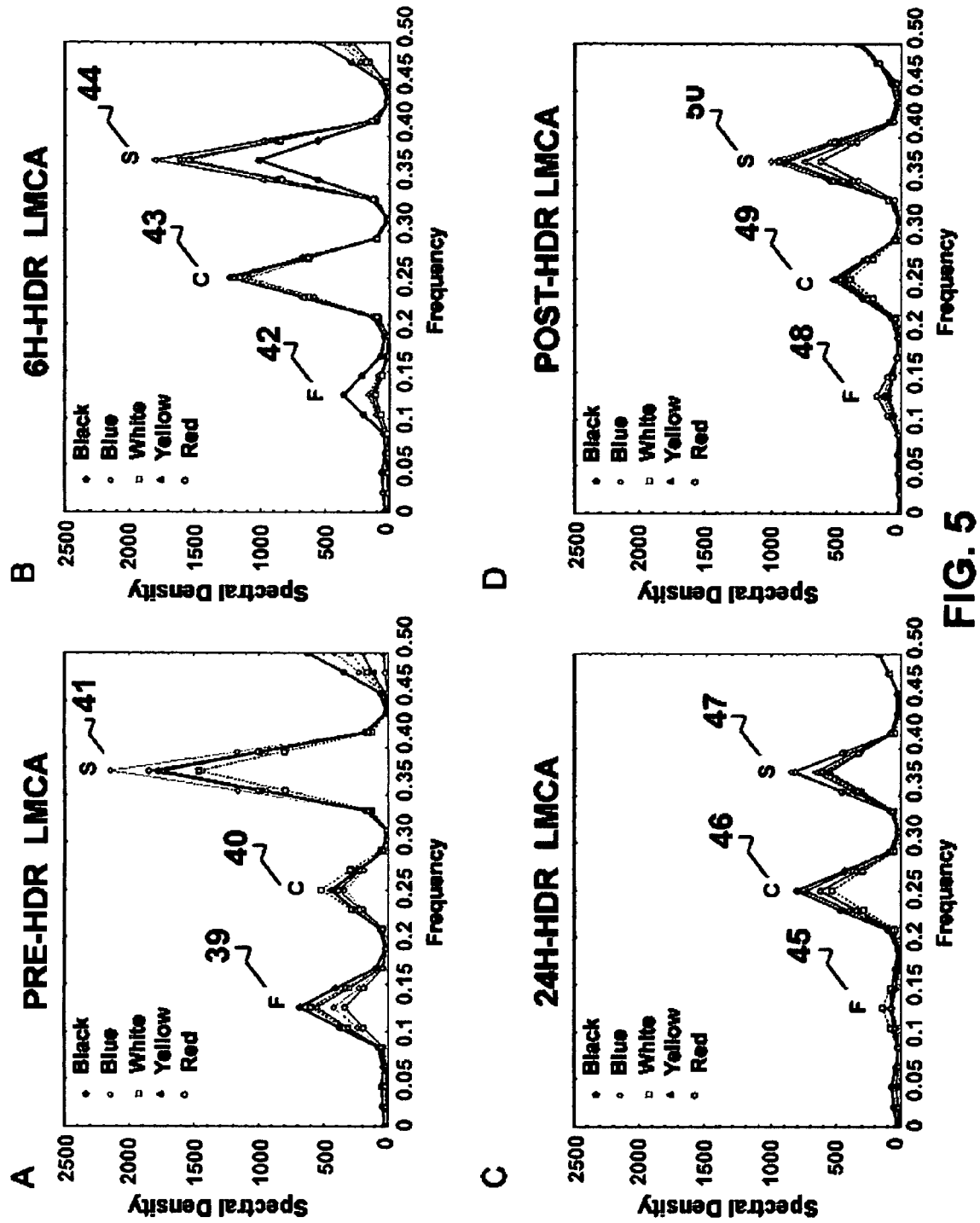
FIG. 5A shows the cortical (C-peak) and subcortical (S-peak) peaks for each color stimulation in the LMCA at Pre-HDR.
FIG. 5B shows the cortical (C-peak) and subcortical (S-peak) peaks for each color stimulation in the LMCA at 6H-HDR.
FIG. 5C shows the cortical (C-peak) and subcortical (S-peak) peaks for each color stimulation in the LMCA at 24H-HDR.
FIG. 5D shows the cortical (C-peak) and subcortical (S-peak) peaks for each color stimulation in the LMCA at Post-HDR.

FIG. 4(A-D) shows the overlaid spectral density estimates, for Black and colors (Blue, White, Yellow and Red), at Pre-HDR (FIG. 4A), 6H-HDR (FIG. 4B), 24H-HDR (FIG. 4C), and Post-HDR (FIG. 4D) in the RMCA. FIG. 5(A-D) shows the overlaid spectral density estimates, for Black and colors (Blue, White, Yellow and Red), at Pre-HDR (FIG. 5A), 6H-HDR (FIG. 5B), 24H-HDR (FIG. 5C), and Post-HDR (FIG. 5D) in the LMCA. The F peaks were absent or significantly attenuated, due to posture in total flexion of the right elbow, which blocked blood flow wave reflections from the finger tips, as subject held the viewing device, during all study conditions, as described in an article by Njemanze P. C., titled "*Cerebral lateralization for facial processing: Gender-related cognitive styles determined using Fourier analysis of mean cerebral blood flow velocity in the middle cerebral arteries*", published in Laterality, 2007; 12: 31-49. Color responses were accentuated at subcortical (S-peak) and cortical (C-peak) peaks.

A single-factor ANOVA analysis with repeated measures was used, to determine WAVELENGTH-encoding, ENERGY-encoding and LUMINANCE effects for the C-peaks and S-peaks, respectively. At Pre-HDR, for C-peaks in the RMCA (FIG. 4A), there was a main effect of ENERGY-encoding, $F(1,6)=5.7$, $p=0.05$. There was no main effect of LUMINANCE, (p=NS). At S-peaks, there was only a tendency for WAVELENGTH-encoding, $F(1,6)=4.6$, $p=0.07$, but no LUMINANCE effect, (p=NS). There was WAVELENGTH-differencing in the right hemisphere. On the other hand, in the LMCA (FIG. 5A), for the C-peaks, there was no main effect of WAVELENGTH-encoding, ENERGY-encoding or LUMINANCE, (p=NS). At S peaks, there was a main effect of ENERGY-encoding, $F(1,6)=5.7$, $p=0.05$. There was a main effect of LUMINANCE, $F(1,6)=6.3$, $p<0.05$. In both right (FIG. 4A) and left hemispheres (FIG. 5A), the C-peaks were lower than S-peaks. There was no luminance or sensory conflicts. There was no WAVELENGTH-differencing in the left hemisphere.

At 6H-HDR, for C-peaks in the RMCA (FIG. 4B), there was only a tendency for a main effect of WAVELENGTH-encoding, $F(1,6)=4.8$, $p=0.07$. There was a main effect of LUMINANCE, $F(1,6)=8.2$, $p<0.05$. At S-peaks, there was no WAVELENGTH-encoding and LUMINANCE main effects, (p=NS). There was no WAVELENGTH-differencing in the right hemisphere. On the other hand, in the LMCA (FIG. 5B), for the C-peaks, there was no main effect of WAVELENGTH-encoding and ENERGY-encoding. However, there was a main effect of LUMINANCE, $F(1,6)=19.9$, $p<0.05$. At S peaks, there was no main effect of WAVELENGTH-encoding and LUMINANCE, (p=NS). There was a luminance sensory conflict. There was no WAVELENGTH-differencing in the left hemisphere. In the RMCA, there was CLTP ($p<0.05$) and SLTD ($p<0.05$). On the other hand, in the LMCA, CLTP and SLTD were absent.

At 24H-HDR, for C-peaks in the RMCA (FIG. 4C), there was no main effect of WAVELENGTH-encoding, (p=NS). There was a main effect of LUMINANCE, $F(1,6)=9.7$, $p<0.05$. At S-peaks, there were no main effects of WAVELENGTH-encoding and LUMINANCE, (p=NS). There was no WAVELENGTH-differencing in the right hemisphere. On the other hand, in the LMCA (FIG. 5C), for the C-peaks, there was a main effect of WAVELENGTH-encoding, $F(1,6)=6.2$, $p<0.05$. There was a main effect of LUMINANCE, $F(1,6)=6.9$, $p<0.05$. At S peaks, there was no main effect of WAVELENGTH-encoding and LUMINANCE, (p=NS). There was a luminance sensory conflict. There was no WAVELENGTH-differencing in the left hemisphere. In the RMCA, there was CLTP ($p<0.05$) and SLTD ($p<0.05$). On the other hand, in the LMCA, CLTP and SLTD were absent.

At POST-HDR, for C-peaks in the RMCA (FIG. 4D), there was a tendency for a main effect of WAVELENGTH-encoding, $F(1,6)=5.4$, $p=0.059$. There was a main effect of LUMINANCE, $F(1,6)=6.9$, $p<0.05$. At S-peaks, there was a main effect of ENERGY-encoding, $F(1,6)=20.3$, $p<0.01$, but there was no LUMINANCE main effect, (p=NS). There was a reversed WAVELENGTH-differencing in the right hemisphere. On the other hand, in the LMCA (FIG. 5D), for the C-peaks, there was a main effect of WAVELENGTH-encoding, $F(1,6)=8.1$, $p<0.05$. There was a main effect of LUMINANCE, $F(1,6)=8.9$, $p<0.05$. At S peaks, there was tendency for ENERGY-encoding $F(1,6)=4.8$, $p=0.07$. There was no LUMINANCE effect, (p=NS). There was a reversed WAVELENGTH-differencing in the left hemisphere. There were luminance and color sensory conflicts. In the RMCA, there were CLTP ($p<0.05$) and SLTD ($p<0.05$). On the other hand, in the LMCA, CLTP and SLTD were absent.

CONCLUSION

This is the first published invention that provides a method for recording LTP and LTD during HDR using fTCDS. The findings could be summarized for each data collection time as follows: 1) at Pre-HDR, the cortical activity was lower than subcortical activity, there was no sensory conflict, rather there was functional specialization, with the right hemisphere involved in wavelength-differencing, and the left hemisphere in energy-encoding and luminance effect responsiveness; 2) at 6H-HDR, in the right hemisphere but not left, there was CLTP and SLTD, there was luminance sensory conflict, and a tendency for wavelength-encoding activity in the right cortical region; 3) at 24H-HDR, in the right hemisphere but not left, there were CLTP and SLTD, there was luminance sensory conflict, and wavelength-encoding activity in the left cortical region; 4) at Post-HDR, in the right hemisphere but not left, there were CLTP and SLTD, there was functional duplication, with a reversed wavelength-differencing and luminance effect responsiveness in both right and left hemispheres, giving rise to sensory conflict for both chromatic and achromatic detectors.

The most intriguing findings of the present study are the presence of CLTP and SLTD, during HDR and Post-HDR in the right hemisphere, which lasted for 25 hours or more, if recording was continued. This is the first noninvasive ultrasound recording of long-lasting cortical potentiation and subcortical depression in the intact human brain, reported in literature. The mechanisms underlying potentiation and depression could be deduced from what is known. It is known that for LTP and LTD to occur, there must be glutamate release as described in a book by Thompson R. F., titled "*Brain: A Neuroscience Primer*", 3rd Edition, published in New York: Worth Publishers, 2000, p. 102-117.

While a preferred embodiment of the present invention is described above, it is contemplated that numerous modifications may be made thereto for particular applications without departing from the spirit and scope of the present invention. Accordingly, it is intended that the embodiment described be considered only as illustrative of the present invention and that the scope thereof should not be limited thereto but be determined by reference to the claims hereinafter provided.

I claim:

1. A noninvasive method for inducing and monitoring long-term potentiation and long-term depression in an intact brain of a human subject, including steps of:
   (a) placing the subject in supine position on a tilt bed with head elevated;
   (b) obtaining subject's resting cerebral blood flow velocity in cerebral arteries using transcranial Doppler instrument with two probes placed on the temples and sample volumes focused on cerebral arteries on both sides;

(c) simultaneously with (b) obtaining the mean blood flow velocity on both pairs of cerebral arteries and processing the obtained mean blood flow velocity data using a microcomputer connected to the Doppler instrument;
(d) testing the subject with psychophysiologic stimuli for a given duration while simultaneously monitoring real-time mean blood flow velocity during each psychophysiologic task for baseline recording;
(e) simultaneously with (d) saving all mean blood flow velocity data in marked files for analysis;
(f) positioning the subject in head-down bed rest for a duration of 24 hours to induce brain processes of long-term potentiation and long-term depression;
(g) selecting time intervals for testing the subject with psychophysiologic stimuli;
(h) testing the subject with stimuli for each selected time interval while simultaneously monitoring in real-time mean blood flow velocity during psychophysiologic task;
(i) simultaneously with (h) saving all mean blood flow velocity data in marked files for analysis;
(j) positioning the subject head-up after 24 hours;
(k) selecting time intervals for testing the subject with psychophysiologic stimuli;
(l) testing the subject with stimuli for each selected time interval while simultaneously monitoring in real-time mean blood flow velocity during psychophysiologic task;
(m) simultaneously with (l) saving all mean blood flow velocity data in marked files for analysis;
(n) applying a periodic time series analysis to the saved mean blood flow velocity data for each stimulus at each given time interval;
(o) calculating the spectral density estimates for each stimulus at each given time interval;
(p) plotting all spectral density estimates for each stimulus at each given time interval and identifying as peaks the frequency regions with the highest estimates;
(q) simultaneously with (p) identifying the peaks that characterize fundamental peripheral vascular changes at the first harmonic;
(r) simultaneously with (q) identifying peaks that characterize cortical processes at the second harmonic;
(s) simultaneously with (r) identifying peaks that characterize subcortical processes at the third harmonic;
(t) overlying plots for all stimuli for each given time interval;
(u) comparing the peaks for all stimuli for each given time interval;
(v) identifying the cortical long-term potentiation peaks for each given time interval as accentuation of the peaks at the second harmonic over that at baseline recording; and
(w) simultaneously with (v) identifying the subcortical long-term depression peaks for each given time interval as attenuation of the peaks at the third harmonic over that at baseline recording.

2. The method of claim 1 wherein the said instrument comprises a transcranial Doppler instrument means to acquire cerebral blood flow velocity waveforms used to calculate mean blood flow velocity.

3. The method of claim 1 further including a tilt bed means for providing head-down bed rest and head up tilt at various angles of head inclination.

4. The method of claim 1 wherein the cerebral blood flow velocity is monitored in response to sensory stimuli.

5. The method of claim 1 wherein the cerebral blood flow velocity is monitored in response to adaptive feeding stimuli.

6. The method of claim 1 wherein the cerebral blood flow velocity is monitored in response to motor stimuli.

7. The method of claim 1 wherein the cerebral blood flow velocity is monitored in response to visual stimuli.

8. The method of claim 1 wherein the cerebral blood flow velocity is monitored in response to specific drug intervention.

9. The method on claim 1 wherein the cerebral blood flow velocity is monitored in abnormalities of adaptive feeding behavior.

10. The method of claim 1 wherein the effects of real microgravity on adaptive feeding behavior are examined.

11. A noninvasive method for inducing and monitoring long-term potentiation and long-term depression in an intact brain of a human subject, including steps of:
(a) placing the subject in supine position on a tilt bed with head elevated at 30 degrees;
(b) obtaining subject's resting cerebral blood flow velocity in the middle cerebral arteries using transcranial Doppler instrument with two probes placed on the temples and sample volumes focused on cerebral arteries on both sides;
(c) simultaneously with (b) obtaining the mean blood flow velocity on both pairs of middle cerebral arteries and processing the obtained mean blood flow velocity data using a microcomputer connected to the Doppler instrument;
(d) testing the subject with psychophysiologic stimuli for 60 seconds while simultaneously monitoring real-time mean blood flow velocity during each psychophysiologic task for baseline recording;
(e) simultaneously with (d) saving all mean blood flow velocity data in marked files for analysis;
(f) positioning the subject in head-down bed rest at −6 degrees;
(g) testing the subject at −6 degrees head-down bed rest position with psychophysiologic stimuli while simultaneously monitoring in real-time the mean blood flow velocity during each psychophysiologic task after six hours from the testing at step (f);
(h) testing the subject after 24 hours in head-down position from the testing at step (f) with psychophysiologic stimuli while simultaneously monitoring in real-time the mean blood flow velocity during each psychophysiologic task;
(i) simultaneously with (h) saving all mean blood flow velocity data in marked files for analysis;
(j) positioning the subject head-up at 30 degrees;
(k) testing the subject after one hour in head-up position from the testing at step (j) with psychophysiologic stimuli while simultaneously monitoring in real-time the mean blood flow velocity during each psychophysiologic task;
(l) saving all mean blood flow velocity data in marked files for analysis;
(m) applying Fourier time series analysis to the saved mean blood flow velocity data for each stimulus at baseline;
(n) applying Fourier time series analysis to the saved mean blood flow velocity data for each stimulus at 6 hours in head-down bed rest position;
(o) applying Fourier time series analysis to the saved mean blood flow velocity data for each stimulus at 24 hours in head-down bed rest position;
(p) applying Fourier time series analysis to the saved mean blood flow velocity data for each stimulus at one hour after return to head-up tilt position;

(q) calculating the spectral density estimates for each stimulus at each given time interval and head position;
(r) plotting all spectral density estimates for each stimulus at each given time interval;
(s) simultaneously with (r) identifying peaks that characterize fundamental peripheral vascular changes at the first harmonic;
(t) simultaneously with (r) identifying peaks that characterize cortical processes at the second harmonic;
(u) simultaneously with (t) identifying peaks that characterize subcortical processes at the third harmonic;
(v) overlying plots for all stimuli for each given time interval;
(w) identifying the cortical long-term potentiation peaks as accentuation above baseline peaks;
(x) simultaneously with (w) identifying the subcortical long-term depression peaks as attenuation below baseline peaks;
(y) administering specific interventions; and
(z) evaluating effects of the interventions on the identified peaks.

12. The method of claim 11 wherein the cerebral blood flow velocity is monitored in response to visual stimulation.

13. The method of claim 11 wherein the cerebral blood flow velocity is monitored in subjects with eating disorders.

14. The method of claim 11 wherein the cerebral blood flow velocity is monitored in subjects with motor disorders.

15. The method of claim 11 wherein the cerebral blood flow velocity is monitored in subjects with memory deficits.

16. The method of claim 11 wherein the cerebral blood flow velocity is monitored in subjects addicted to drugs.

17. The method of claim 11 wherein the cerebral blood flow velocity is monitored in subjects with chronic pain.

18. A noninvasive method for inducing and monitoring long-term potentiation and long-term depression in an intact brain of a primate subject, including steps of:
(a) placing the subject in supine position on a tilt bed with head elevated;
(b) obtaining subject's resting cerebral blood flow velocity in cerebral arteries using transcranial Doppler instrument with two probes placed on the temples and sample volumes focused on cerebral arteries on both sides;
(c) simultaneously with (b) obtaining the mean blood flow velocity on both pairs of cerebral arteries and processing the obtained mean blood flow velocity data using a microcomputer connected to the Doppler instrument;
(d) testing the subject with psychophysiologic stimuli for a given duration while simultaneously monitoring real-time mean blood flow velocity during each psychophysiologic task for baseline recording;
(e) simultaneously with (d) saving all mean blood flow velocity data in marked files for 1 analysis;
(f) positioning the subject in head-down bed rest;
(g) selecting time intervals for testing the subject with psychophysiologic stimuli;
(h) testing the subject with stimuli for each selected time interval while simultaneously monitoring in real-time the mean blood flow velocity during each psychophysiologic task;
(i) simultaneously with (h) saving all mean blood flow velocity data in marked files for analysis;
(j) positioning the subject in head-up bed rest;
(k) selecting time intervals for testing the subject with psychophysiologic stimuli;
(l) testing the subject with stimuli for each selected time interval while simultaneously monitoring in real-time the mean blood flow velocity during each psychophysiologic task;
(m) simultaneously with (1) saving all mean blood flow velocity data in marked files for analysis;
(n) applying a periodic time series analysis to the saved mean blood flow velocity data for each stimulus at each given time interval;
(o) calculating the spectral density estimates for each stimulus at each given time interval;
(p) plotting all spectral density estimates for each stimulus at each given time interval;
(q) simultaneously with (p) identifying peaks that characterize fundamental peripheral vascular changes at the first harmonic;
(r) simultaneously with (q) identifying peaks that characterize cortical processes at the second harmonic;
(s) simultaneously with (r) identifying peaks that characterize subcortical processes at the third harmonic;
(t) overlying plots for all stimuli for each given time interval;
(u) comparing the peaks for all stimuli for each given time interval;
(v) identifying the cortical long-term potentiation peaks accentuated above baseline peaks;
(w) simultaneously with (v) identifying the subcortical long-term depression peaks attenuated below baseline peaks;
(x) administering specific phychoactive drug interventions;
(y) repeating the aforementioned steps (a-w); and
(z) evaluating the effects of the specific interventions.

* * * * *